United States Patent
Crockford (10) Patent No.: US 9,332,919 B2
(45) Date of Patent: May 10, 2016

(54) HEART MONITORING APPARATUS

(71) Applicant: Cardiocity Limited, Colchester (GB)

(72) Inventor: Chris Crockford, Colchester (GB)

(73) Assignee: Cardiocity Limited, Colchester (GB)

( * ) Notice: Subject to any disclaimer, the term of this patent is extended or adjusted under 35 U.S.C. 154(b) by 100 days.

(21) Appl. No.: 13/886,541

(22) Filed: May 3, 2013

(65) Prior Publication Data
US 2013/0245480 A1 Sep. 19, 2013

Related U.S. Application Data (63) Continuation of application No. PCT/EP2012/056243, filed on Apr. 4, 2012.

(30) Foreign Application Priority Data

| Apr. 4, 2011 | (GB) | 1105699.1 |
| Oct. 10, 2012 | (GB) | 1218223.4 |

(51) Int. Cl.
| A61B 5/0404 | (2006.01) |
| A61B 5/0452 | (2006.01) |
| A61B 5/00 | (2006.01) |
| A61B 5/0408 | (2006.01) |

(52) U.S. Cl.
CPC .......... *A61B 5/0404* (2013.01); *A61B 5/0408* (2013.01); *A61B 5/0452* (2013.01); *A61B 5/6825* (2013.01); *A61B 5/6892* (2013.01); *A61B 5/721* (2013.01); *A61B 2562/0219* (2013.01)

(58) Field of Classification Search
CPC .... A61B 5/6825; A61B 5/6892; A61B 5/721; A61B 5/0408; A61B 5/0402; A61B 5/0404
See application file for complete search history.

(56) References Cited

U.S. PATENT DOCUMENTS

| 5,337,753 A | * | 8/1994 | Lekhtman | ........... A61B 5/0245 600/519 |
| 5,365,935 A | * | 11/1994 | Righter et al. | ................. 600/523 |

(Continued)

FOREIGN PATENT DOCUMENTS

| DE | 102005048496 A1 | 4/2007 |
| EP | 1627597 A1 | 2/2006 |

(Continued)

OTHER PUBLICATIONS

Mehta S.S. et al., "Detection of P and T-waves in Electrocardiogram," Proc. World Congress on Engineeing and Computer Science, San Francisco, 2008, pp. 1147-1152.

(Continued)

*Primary Examiner* — Michael Kahelin
(74) *Attorney, Agent, or Firm* — Kenta Suzue; Haynes Beffel & Wolfeld LLP (57) ABSTRACT

An electrocardiographic device for sensing cardiac activity in a user, the electrocardiographic device comprising: plurality of electrodes provided at a surface of the device for electrical engagement with a pair of extremities of a user; one or more movement sensors arranged to, in use, detect movement of a user's extremities; and a control unit configured to receive electrical signals from the electrodes and to, in use, process said signals in dependence on the output of the one or more movement sensors so as to filter variations from the signals due to movement of the user's extremities.

39 Claims, 3 Drawing Sheets

(56) References Cited

U.S. PATENT DOCUMENTS

| | | | |
|---|---|---|---|
| 5,613,495 A * | 3/1997 | Mills et al. | 600/509 |
| 6,912,414 B2 * | 6/2005 | Tong | 600/372 |
| 7,949,389 B2 | 5/2011 | Wolfberg et al. | |
| 2002/0045805 A1 | 4/2002 | Gopinathan et al. | |
| 2003/0171661 A1 | 9/2003 | Tong | |
| 2007/0149888 A1 | 6/2007 | Kohls et al. | |
| 2007/0156190 A1 | 7/2007 | Cinbis | |
| 2007/0197925 A1 | 8/2007 | Moore | |
| 2007/0260151 A1 | 11/2007 | Clifford | |
| 2009/0048526 A1 * | 2/2009 | Aarts et al. | 600/508 |
| 2010/0049068 A1 | 2/2010 | Fuwamoto et al. | |
| 2010/0125185 A1 | 5/2010 | Kuo et al. | |
| 2010/0137727 A1 | 6/2010 | Sameni et al. | |
| 2010/0292589 A1 | 11/2010 | Goodman | |
| 2012/0172729 A1 | 7/2012 | Yi et al. | |

FOREIGN PATENT DOCUMENTS

| | | |
|---|---|---|
| GB | 2479255 A | 10/2011 |
| GB | 2489704 A | 10/2012 |
| JP | 2006231020 A | 9/2006 |
| WO | 0116607 A2 | 3/2001 |
| WO | 2005/048824 A2 | 6/2005 |
| WO | 2011031062 A2 | 3/2011 |

OTHER PUBLICATIONS

Sun Y. et al., "Characteristic wave detection in ECG signal using morphological transform," BMC Cardiovascular Disorders, vol. 28:5, 2005, 7 pp. (online only—open access—no further pagination) BMC Cardiovasc Disord. 2005; 5: 28. Published online Sep. 20, 2005. doi: 10.1186/1471-2261-5-28 <<http://dx.doi.org/10.1186%2F1471-2261-5-28>>.

Lian et al., "A simple method to detect atrial fibrillation using RR intervals," Am. Jour. Cardiology, vol. 107:10, 2011, pp. 1494-1497.

Hamilton P.S. et al., "Quantitative investigation of QRS detection rules using the MIT/BIH arrhythmia database," IEEE Transactions on Biomedical Engineering, vol. BME-33:12, 1986, pp. 1157-1165.

International Search Report mailed Aug. 28, 2012 in related application PCT/EP2012/056243, 5 pp.

Search report dated Oct. 20, 2011 in related application GB1105699.1, 2 pp.

Search Report dated Oct. 11, 2013 for related application GB 1218223.4; 7 pages.

Communication dated May 7, 2014 of corrected version of search report of Oct. 10, 2013 for related GB 1218223.4; 4 pages.

* cited by examiner

HEART MONITORING APPARATUS

RELATED APPLICATIONS

This application is a continuation of PCT/EP2012/056243, filed 4 Apr. 2012, which claims foreign priority under 35 USC 119(a) to GB 1105699.1 filed 4 Apr. 2011. This application also claims foreign priority under 35 USC 119(a) to GB 1218223.4, filed 10 Oct. 2012.

BACKGROUND OF THE INVENTION

The present invention relates to methods and apparatus for the acquisition and interpretation of ECG signals.

The use of electrocardiogram (ECG) detection and monitoring equipment has become pervasive, with ECGs being used to determine cardiac electrical activity of both animals and humans. ECG equipment is used for a variety of purposes: from measuring the cardiac performance of athletes, to observing basic heart function, through to the detailed monitoring of problems in specific sections of the cardiac system.

Long term ECG monitoring is an established practice, and the detection of the heart's rhythm when monitored over time can identify performance problems known as arrhythmias that can be classified according to the area of the cardiac system that has caused the rhythm to be disrupted. Short term monitoring can provide a means to understand momentary cardiac performance but will not provide a full insight into what may subsequently happen to the cardiac system.

Conventional ECG equipment monitors the electrical activity at the skin of a subject due to the beating of the heart and expresses the electrical activity as a waveform (an electrocardiogram). The electrical activity is detected by electrodes (typically Ag/AgCl electrodes) attached at specific points on a subject's anatomy and electrically coupled to the skin by a conductive gel. Modern ECG systems can make use of automated algorithms that analyse the structure, timing, and electrical characteristics of the cardiac systems various components.

The placement of the electrodes is conventionally determined in accordance with Einthoven's Triangular law, which allocates three electrodes as limb leads: Left Hand (LH), Right Hand (RH), and Left Foot (LF). The potential difference (typically millivolts) between LH and RH, being known as Lead 1, between LH and LF as Lead 2, and RH and LF as Lead 3. The term lead is used to refer to a conceptual investigative lead and not a physical electrode cable lead. By taking readings from the three limb leads it is possible to understand the electrical activity of the cardiac system from three angular perspectives. If the average of any two leads is then further compared against the third lead, it is possible to derive a further three investigative leads, known as the derived Leads 4-6.

A 6 lead systems allows an investigator to see a cardiac system's electrical activity from the centre of the source of the electrical signal along six different axes. To understand the effect of the electrical signal on specific muscle tissues of the cardiac system, further investigative leads (chest leads) must be attached to the body to look at the electrical signal passing through the regions of the heart. The deployment of chest leads (known as V1 through V6) in an arc from approximately the sternum to under the left hand side of the rib cage allows such a detailed reading of the electrical activity passing sequentially through the muscles of the heart. This allows various diseases, conditions and any damage to the heart to be determined.

Variations on the placement of leads has led to more derived leads being obtained through fewer electrodes, and various algorithms have been established to enable fewer electrodes to yield more information about the electrical activity of the cardiac system.

The algorithms used to identify different rhythm problems, or arrhythmias, use time based analysis of the outputs from the electrodes and care must be used to ensure that the correct time base is used when comparing one electrode's signal with another. The time stamping of individual signals can require a highly accurate and correlated time source.

The placement of conventional conducting electrodes on the subject often causes issues, especially if the subject is hairy or has a skin condition that causes the subject's skin to react to the adhesive pad. Conductive gels can also cause irritation to the subject and also introduce the problem that the gel can provide low resistance paths between adjacent electrodes.

Recently, "contactless" electrodes have been introduced that measure electrical potential at the skin without a direct electrical contact by means of capacitive coupling. These electrodes, commonly referred to as electric potential sensors, work by sensing the electric field created by displacement currents in the body of the subject. These electric potential sensors are discussed in International Patent Application Publication No. WO 01/16607, which describes an electric field sensor having a capacitive pick-up electrode for the detection of alternating electrical fields originating from within the human body. The electrode is connected to a high impedance sensing amplifier. In order to render the capacitance coupling relatively sensitive to variations in the separation between the body and the electrode, the electrode itself is separated from the body by a thin (preferably low dielectric) insulating layer, and a limiting capacitor is placed in series with the input to the sensing amplifier. Thus the sensor can be seen to be contactless.

Such electric potential sensors have promised to allow ECGs to be acquired without the need for taping or conductive gels as with conventional electrodes. However, the level of noise present in electrical signals acquired by means of electric potential sensors is a problem and there remains a need for ECG sensors that do not need to be carefully located on a patient by a skilled healthcare practitioner and that allow an ECG to be rapidly acquired with minimal inconvenience to the patient.

SUMMARY OF THE INVENTION

According to a first aspect of the present invention there is provided an electrocardiographic device for sensing cardiac activity in a user, the electrocardiographic device comprising:
  a plurality of electrodes provided at a surface of the device for electrical engagement with a pair of extremities of a user;
  one or more movement sensors arranged to, in use, detect movement of a user's extremities; and
  a control unit configured to receive electrical signals from the electrodes and to, in use, process said signals in dependence on the output of the one or more movement sensors so as to filter variations from the signals due to movement of the user's extremities.

The plurality of electrodes preferably comprises a first set of one or more electrodes for engagement with a first extremity of a user and a second set of one or more electrodes for engagement with a second extremity of a user, the first set of electrodes having an associated first movement sensor arranged to detect movement of the first extremity and the second set of electrodes having an associated second movement sensor arranged to detect movement of the second extremity, the control unit being configured to perform filtering of signals from the first and second sets of electrodes in dependence on the output from the respective movement sensor.

Preferably said filtering comprises cancellation or suppression of features in electrical signals from the electrodes that are common to both the signals from the electrodes and the output of the one or more movement sensors.

Preferably the control unit is configured to provide said filtered electrical signals at an output of the device.

Preferably the output of the one or more movement sensors represents motion and/or vibration of the user's extremities. Preferably the one or more movement sensors include one or more of an accelerometer, a strain gauge, a microphone and a pressure sensor.

Preferably the electrodes of the set are provided at two electrically insulating user interaction regions of the electrocardiographic device, each user interaction region being adapted for engagement with an extremity of a user.

Preferably each user interaction region comprises a layer of shape memory foam for engagement with a user's extremity, the electrodes being provided at the shape memory foam.

Preferably each user interaction region is supported on a floating plate elastically coupled to the body of the electrocardiographic device. Preferably each user interaction region is coupled to the body of the electrocardiographic device by a damping mechanism arranged to dissipate kinetic energy due to motion of the floating plate relative to the body of the electrocardiographic device.

Both user interaction regions could be supported at the same floating plate.

Preferably each floating plate is elastically coupled to the body of the electrocardiographic device by one or more of: elastic springs, resilient rubber or plastic members, and elastic foam.

Preferably the set of electrodes of the device are provided for electrical engagement with the hands of a user and the device comprises a set of indicia indicating an intended position for a user's hands on the device, the set of electrodes being arranged relative to the set of indicia such that, in use when a user's hands are in the intended position, at least one electrode is located under the thenar eminence or the hypothenar eminence of each of the user's hands.

Suitably the indicia comprise a graphical pair of hands indicating the intended position of a user's hands relative to the electrodes and/or indentations on the surface of the device indicating the intended position of a user's hands relative to the electrodes.

The electrocardiographic device could further comprise a second set of indicia indicating a second intended position of a user's hands with respect to the electrodes; wherein the electrodes are arranged relative to the second set of indicia such that, in use when a user's hands are in the second intended position, at least one electrode is located under the medial side of the hypothenar eminence of each of the user's hands.

Suitably the set of electrodes of the device are provided for electrical engagement with the feet of a user and the device comprises a set of indicia indicating an intended position for a user's feet on the device, the set of electrodes being arranged relative to the set of indicia such that, in use when a user's feet are in the intended position, at least one electrode is located under the heel pad of each of the user's feet.

The electrocardiographic device could further comprise a display screen operable to display an electrocardiograph acquired by the electrodes.

Suitably the electrocardiographic device is configured to be foldable along one or more folds such that, when folded, the device is operable to present at least one of the electrodes on each of two outward-facing surfaces of the device, the two outward-facing surfaces being separated by at least one fold. Suitably the electrocardiographic device is provided in the form of a book having one or more pages, at least one of the electrodes being provided at the front and rear inside covers of the book. The pages of the book could provide instructions for use of the electrocardiographic device.

The electrocardiographic device preferably further comprises one or more inputs for receiving signals from wearable conducting electrodes or electric potential sensors, the control unit being operable to combine said one or more inputs with the signals from the set of electrodes so as to form representations of one or more multi-lead ECGs. The inputs could be wired or wireless inputs.

According to a second aspect of the present invention there is provided an electrocardiographic system comprising:
 a first electrocardiographic device as described herein; and
 a data processing unit configured to process signals from the electrodes of the first electrocardiographic device so as to form an electrocardiogram and/or diagnose cardiac abnormalities.

The data processing unit could be one or more of a personal computer, handheld computer, smartphone, server, or a processing unit of the electrocardiographic device itself.

Suitably the electrocardiogram is a Lead I electrocardiogram.

Preferably the electrocardiographic system further comprises one or more wearable biosensors and the data processing unit is further configured to process signals from the wearable biosensors so as to form an electrocardiogram in dependence on signals from both the wearable biosensors and the electrodes of the first electrocardiographic device.

The wearable biosensors could be electric potential sensors or conducting electrodes.

Preferably the wearable biosensors are provided in clothing and/or as straps adapted for engagement with a limb or extremity of a user.

Suitably the electrocardiographic system further comprises a second electrocardiographic device as claimed in any of claims 1 to 22, and the data processing unit is further configured to process signals from the electrodes of the second electrocardiographic device so as to form an electrocardiogram in dependence on signals from electrodes of both the first and second electrocardiographic devices. Suitably the electrocardiogram includes a Lead II and/or III electrocardiogram.

Preferably the data processing unit is configured to characterise an electrocardiogram according to a predetermined set of cardiac parameters, including one or more of: amplitude and duration of a detected QRS complex, ventricular activation time, relative amplitude and timings of the Q, R and S peaks, R-R interval, QT interval, P wave timing relative to the QRS complex, and T wave to P wave smoothness.

Preferably the data processing unit is configured to diagnose cardiac abnormalities in dependence on the predetermined set of cardiac parameters.

Preferably the data processing unit is configured to diagnose cardiac abnormalities in dependence on a comparison of the cardiac parameters of the electrocardiogram with a set of stored cardiac parameters.

Preferably the data processing unit is configured to, on detecting one or more features indicative of cardiac abnormalities in the electrocardiogram, provide the electrocardiogram to a healthcare professional for further analysis and/or indicate to the user that the advice of a healthcare professional should be sought.

The electrocardiographic system could further comprise a data store accessible to the data processing unit, the data processing unit being configured to store the predetermined set of cardiac parameters at the data store and optionally a digital representation of signals from the electrodes along with, optionally, a digital representation of output(s) of the movement sensor(s).

Preferably the data processing system is configured to instruct the user to connect at least one wearable biosensor and/or a second electrocardiographic device as claimed in any of claims 1 to 22 if one or more of the following is true: one or more features characteristic of a cardiac abnormality are detected in the electrocardiogram; signals from the electrodes of the first electrocardiographic device or the electrocardiogram itself includes characteristics indicative of a poor signal; and one or more expected characteristics of cardiac activity are absent or only weakly present in the electrocardiogram.

Preferably the expected characteristics of cardiac activity include a P wave.

Preferably the data processing unit is configured to instruct the user by means of a display screen at the first electrocardiographic device.

Preferably the first and second sets of electrodes of the first electrocardiographic device each comprise a plurality of electrodes and the data processing unit is configured to (i) form a measure of the quality of the differential signal from each pair of electrodes that includes one electrode from the first set and one electrode from the second set, and (ii) select that pair of electrodes that has the highest quality measure as the Lead I signal.

Preferably the data processing system is configured to process signals from the electrodes in accordance with a QRS detection algorithm and, if the amplitude of the QRS complex is determined to exceed the noise floor by greater than a predetermined amount then a P wave algorithm is used for subsequent analysis of the electrocardiogram, otherwise an R-R interval algorithm is used for subsequent analysis of the electrocardiogram.

An electrocardiographic device as described herein could be configured to acquire an electromyogram of one or more muscles of a user.

An electrocardiographic system as described herein could be configured to acquire an electromyogram of one or more muscles of a user, the system including one or more wearable biosensors and the data processing system being configured to control apparatus for electrical stimulation of said one or more muscles.

According to a third aspect of the present invention there is provided a method for acquiring an electrocardiogram by means of an electrocardiographic system comprising an electrocardiographic device having a plurality of electrodes adapted for engagement with a user, the method comprising:
  capturing a representation of the cardiac activity of a user by means of the plurality of electrodes;
  at a data processing device of the electrocardiographic system, processing the representation of the cardiac activity so as to identify whether it includes characteristics indicative of a poor signal;
  if the processing step identifies characteristics indicative of a poor signal, indicating to the user by means of a display screen at the electrocardiographic device a preferred engagement of the user with the electrocardiographic device; and
  subsequently, acquiring an electrocardiogram in dependence on signals from the electrodes of the electrocardiographic device.

According to a fourth aspect of the present invention there is provided a method for acquiring an electrocardiogram by means of an electrocardiographic system comprising a first electrocardiographic device having a plurality of electrodes adapted for engagement with a pair of hands, the method comprising:
  capturing a representation of the cardiac activity of a user by means of the plurality of electrodes;
  at a data processing device of the electrocardiographic system, comparing the representation of the cardiac activity of the user with a set of predetermined characteristics of cardiac activity and identifying whether one or more of the following conditions is true: one or more characteristics indicative of a cardiac abnormality are present in the representation of the cardiac activity; the representation of the cardiac activity includes characteristics indicative of a poor signal; and one or more expected characteristics are absent or only weakly present in the representation of the cardiac activity;
  in response to identifying that one or more of the conditions is true, indicating to the user to connect into the electrocardiographic system one or more wearable electrodes and/or a second electrocardiographic device having a plurality of electrodes adapted for engagement with a pair of feet; and
  acquiring an electrocardiogram in dependence on signals from the electrodes of the first electrocardiographic device and the one or more wearable electrodes and/or the second electrocardiographic device.

Preferably the characteristics indicative of a poor signal include a predetermined noise level.

Preferably the expected characteristics include a P wave.

According to a fifth aspect of the present invention there is provided a method for analysing an electrocardiogram by means of an electrocardiographic system comprising an electrocardiographic device having a plurality of electrodes adapted for engagement with a user, the method comprising:
  acquiring an electrocardiogram by means of the plurality of electrodes;
  at a data processing device of the electrocardiographic system, processing the electrocardiogram in accordance with a QRS detection algorithm in order to identify the amplitude of the QRS complex in the electrocardiogram relative to its noise floor;
  if the amplitude of the QRS complex is determined to exceed the noise floor by greater than a predetermined amount, selecting a P wave algorithm for subsequent analysis of the electrocardiogram, and otherwise selecting an R-R interval algorithm for subsequent analysis of the electrocardiogram; and
  analysing the electrocardiogram using the selected algorithm.

According to a sixth aspect of the present invention there is provided a method for acquiring an electrocardiogram by means of an electrocardiographic system comprising an electrocardiographic device having first and second sets of electrodes, each set of electrodes being arranged for engagement with a different one of a pair of extremities of a user, the method comprising:
  for each of a predetermined series of pairs of electrodes, forming a measure of the quality of the differential signal from the pair of electrodes, each pair of electrodes including one sensor from the first set and one sensor from the second set:
selecting the pair of electrodes having the highest measure of signal quality; and
acquiring an electrocardiogram by means of the selected pair of electrodes of the first electrocardiographic device.

According to a seventh aspect of the present invention there is provided an electrocardiographic device for sensing cardiac activity in a user comprising:
a plurality of electrodes; and
a set of indicia indicating an intended position of a pair of hands of a user with respect to the electrodes;
wherein the electrodes are arranged relative to the set of indicia such that, in use when a user's hands are in the intended position, an electrode is located under the thenar eminence and/or the hypothenar eminence of each of the user's hands.

DESCRIPTION OF THE DRAWINGS

The present invention will now be described by way of example with reference to the accompanying drawings, in which.

DETAILED DESCRIPTION OF THE DRAWINGS

The following description is presented to enable any person skilled in the art to make and use the invention, and is provided in the context of a particular application. Various modifications to the disclosed embodiments will be readily apparent to those skilled in the art.

The general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Conventional teaching suggests that due to the low sensitivity of conducting electrodes and the nature of the electrical signals generated by cardiac activity, it is not possible to acquire good quality ECGs without careful positioning of the electrodes and the use of conductive gel. However, the inventor of the present invention has surprisingly discovered that conventional conducting electrodes can be used in particular locations at the extremities of the body without conductive gel to acquire good quality ECGs, and the performance of such a system can be significantly boosted through the use of filtering and various optimisation algorithms. Furthermore, although on the face of it being able to acquire ECGs with a good electrical contact to the body, electric potential sensors have been found to yield noisy data due to their sensitivity.

The inventor has established that the optimum location for electric potential sensors at the extremities of the body is in fact very similar to the optimum location for conventional conducting electrodes, with ECG apparatus configured as described herein being able to make use of either conventional electrodes or electric potential sensors in order to acquire good quality ECGs. The term "electrodes" is used herein to refer to both conventional electrodes and electric potential sensors, as well as any functionally equivalent sensor technologies by means of which electrical activity of the body can be measured.

Figure 1:
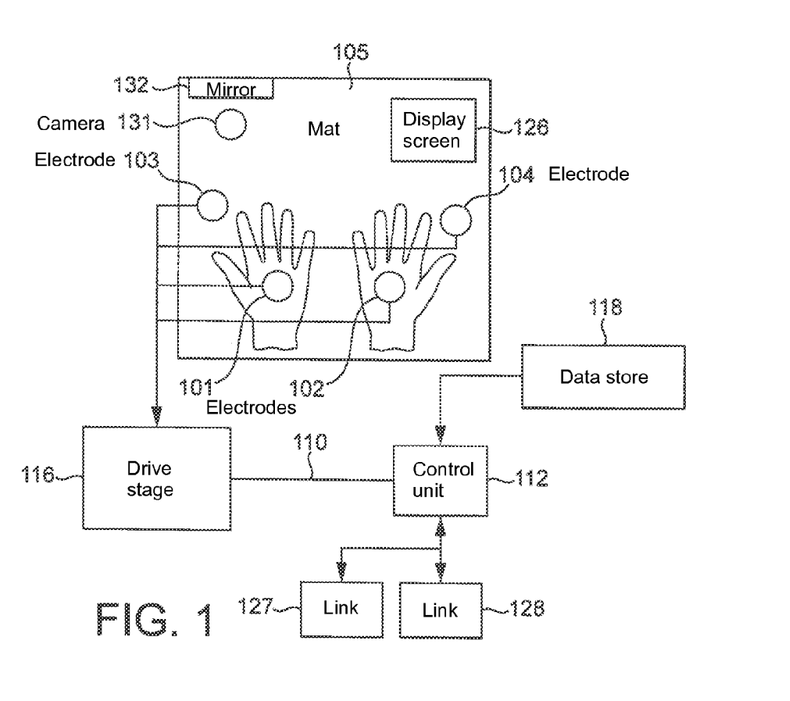
FIG. 1 is a schematic diagram of an electrocardiographic device for sensing cardiac activity in a user in accordance with the present invention.

A schematic diagram of an electrocardiographic system comprising an electrocardiographic device for sensing cardiac activity in a user is shown in FIG. 1. The two hands are shown by way of illustration only and are an example of one use of the electrocardiographic device. The electrocardiographic device includes electrodes 101 and 102, and optionally electrodes 103 and 104. Electrodes 101 and 102 are set into an insulating mat 105 which preferably includes one or more sets of indicia indicating where on the mat the user is intended to place their hands and/or feet (the case of hands is illustrated in FIG. 1).

A mat could comprise sets of indicia for both hands and feet so as to allow a mat to be used to acquire ECG signals from either hands or feet. These indicia may be in the form of outline shapes showing where the hands/feet should be placed, and/or indentations in the surface of the mat showing where the hands/feet should be placed. Most advantageously, the mat is configured such that: (a) in the case of hands: the hands of a user are placed so that at least electrodes 101 and 102 lie under the thenar eminence and/or hypothenar eminence of each hand when in use, with the palms face-down on the mat; and (b) in the case of feet: the feet of a user are placed so that at least electrodes 103 and 104 lie under the heel pad of each foot when in use, with the feet soles-down on the mat. This helps to shield the sensors from environmental noise.

Electrodes 101 to 104 could be any kind of conducting electrode arranged for direct contact with the skin of a user, or electric potential sensors. The electrodes could be, for example, metallic pads, such as a copper disc set into the surface of the mat.

The signal from each electrode would typically be amplified by drive stage electronics 116. For example, a Texas Instruments MSP430 microcontroller can be implemented to provide the necessary amplification and drive stage signal processing. Digital data representing the output from the electrodes is then provided to a control unit 112 over link 110.

The electrocardiographic device comprises a control unit 112 for processing the signals from the electrodes so as to form one or more differential signals representative of electrical activity of the user's heart. Such processing could include filtering and other signal processing steps. The control unit could further process the differential signals into an ECG trace and/or perform electrocardiogram analysis so as to identify characteristics of the user's ECG and potentially any heart conditions. For example, the electrode signals could be processing in accordance with a set of algorithms stored at data store 118 (preferably local to the control unit) for identifying arrhythmias. Control unit 112 could include drive stage 116.

Preferably the processing of the differential signals to form an ECG trace and characterise the user's ECG is performed at another device, such as a data processing unit connected to the control unit by means of wireless or wired links 127 and 128. The data processing unit could be, for example, a laptop, smartphone, or internet server accessible to the electrocardiographic device. Thus different aspects of the filtering, signal processing and electrocardiogram analysis could be performed at different parts of the combination of the control unit at the electrocardiographic device itself and a data processing unit coupled to the device. In preferred embodiments, signal filtering and conditioning is performed at the electrocardiographic device and electrocardiogram analysis is performed at a connected computer, with the option of uploading data to a server for more rigorous analysis should the need arise. Link 110 could be any kind of wired or wireless connection, such as a serial bus, Ethernet link or Bluetooth connection.

Electrocardiogram analysis is performed so as to process the data representing the output from the sensors in the manner required by the application—e.g. to provide an ECG trace, output a statistical analysis of the ECG rhythm strips, or provide indications of any cardiac abnormalities detected by the processing. The output 129 from the control unit or data processing unit may be in the form of a set of one or more rhythm strips of ECG data. The output could be stored at the data store 118 and/or displayed at display screen 126. The screen could be used to provide instructions to the user. The screen may be integral to mat 105 or could be provided separately. The wireless interface 127 may provide telephonic interfaces such as GSM or 3G, or other radio interfaces such as Bluetooth or WiFi.

The electrodes 101 to 104 are provided at the device such that, in use, the skin of a user is in direct contact with the electrodes.

In the example shown in FIG. 1, a mat or pad is provided onto which the subject under investigation can arranged their hands upon electrodes 101 and 102 in order to allow a single Lead I ECG reading to be recorded as the potential difference between electrodes 101 and 102. The mat or pad 105 could be provided with additional sensors 103, 104 in order to capture ECG readings from additional body parts. These sensors could be integral with the mat or (not shown in the figure) connected to the mat by wired or wireless connections. Wearable sensors connected into the ECG device could comprise conducting electrodes but would preferably comprise electric potential sensors. For example, sensors 103, 104 could be EP sensors provided as devices adapted for attachment to a patient, such as a velcro strap comprising one or more EP sensors for connection around a wrist or ankle, or a chest harness comprising a plurality of EP sensors, to give two examples. The mat could be configured so as to capture readings from all sensors and electrodes simultaneously. The provision of multiple sets of sensors allows a mat to be used in multiple configurations—for example, to take 1-lead readings from either a pair of hands, a pair of feet, or a foot and a hand, or to take multiple lead readings from a combination of hands, feet or other parts of the body.

Additional electrodes could be provided by another mat configured in accordance with the present invention, the two mats being connected together so as to allow the differential processing of pairs of electrodes. The mats could be connected together at a data processing unit such as a laptop, or at control unit 112. For example, a user could stand on one mat and engage one or more feet with feet electrodes 103 and 104, whilst engaging their hands with electrodes 101 and 102 of a second mat. This allows ECG leads 1 to 3 to be obtained, and hence the derivation of leads 4 to 6.

Electrodes configured in accordance with the present invention can be located at the limbs of a subject so as to capture multi-lead ECG signals in an equivalent manner to conventional multi-lead ECG systems having electrodes located at the same positions, but with the benefits that no careful positioning is required by a skilled healthcare worker, the patient is not required to expose their chest to allow connection of the electrodes, and adhesives or conductive gels are not required.

It is particularly advantageous that the parts of the user's anatomy that are placed on the mat are arranged such that the user's anatomy shields the electrodes from environmental noise. This can improve the fidelity and speed of detection of the ECG system. For example, the positioning of the hand such that the thenar eminence or hypothenar eminence of the hand is located over an electrode has been found to allow a good ECG signal to be captured and allows the thick, fleshy part of the hand to shield the electrode from environmental noise. This speeds up ECG acquisition time and lowers noise levels present in the signal. The positioning of a foot such that the heel or ball of the foot (preferably at the base of the big toe) lies over an electrode is similarly advantageous and it is preferable if a mat adapted for use with a user's feet is provided with indicia such that in use the user is directed to engage with the electrodes in such an advantageous manner.

It is advantageous if a feedback system is provided for use with the mat so as to ensure that the limbs of a user are placed in their optimal positions in order to best shield electrodes from environmental noise. When ECG signals are acquired by the mat but those signals are of poor quality, the control unit 112 is preferably configured to alert the user to the fact that their limbs may not be optimally placed on the mat and/or to indicate to the user to add one or more additional electrode mats or wearable sensors so as to provide additional leads and/or to indicate to the user to engage with different electrodes of the mat. The control unit can determine whether a signal is poor quality by comparing an acquired ECG signal with sets of characteristics stored at data store 118, at least some of which indicate that there is poor engagement between the user and the respective electrodes.

As is known in the art, the mat is configured to use a QRS detection algorithm to identify the heart beats in the signal from the electrodes. This allows the amplitude of the QRS complex and the timing between features of the ECG to be established, along with measures of the noise in the signal. Further refinements can also be employed to improve the quality of the signal, such as filtering, use of a baseline wander algorithm to better track the varying signal and use of cubic spline operations to stabilise the ECG.

Various aspects of the ECG of a user can be used to both characterise the ECG and hence heart function, and allow the quality of the captured ECG to be determined. Characterisation of the ECG allows the ECG to be stored as a set of parameters describing the ECG and can be used for later analysis or for comparison against subsequently-captured ECGs. Suitable aspects of the ECG that can be stored for comparison or for determining quality include:
1. Amplitude and timing of the QRS complex (this could include, absolute amplitude of the R peak, absolute or relative amplitudes of the Q and S peaks, duration of the QRS complex, ventricular activation time, absolute or relative timings of the Q, R and S peaks);
2. R-R interval (i.e. the user's pulse);
3. QT complex (this represents the electrical depolarization and repolarization of the left and right ventricles);
4. P wave timing relative to the QRS complex (this is most easily identified from Lead II, which can be captured from the differential signal from an electrode at the right hand and an electrode at the left foot;
5. T wave to P wave smoothness (the presence of bumps—i.e. a low smoothness—can indicate atrial fibrillation, although this diagnosis is best confirmed by taking a multiple lead ECG).

A low quality signal can be indicated if, amongst other things, the QRS complex cannot be identified, if its amplitude is small, if significant variation is observed in any of the above characteristics that is unlikely to be due to the cardiac activity of the user, or if a significant noise level is observed in the signal.

Discussions of signal filtering and quality determination suitable for use in the systems described herein are set out in the following US patent applications, all of which are herein incorporated by reference in their entirety: Ser. Nos. 11/470, 506; 12/624,175; and 12/424,046.

Preferably the control unit directs the user to adjust the placement of their limbs (e.g. hands or feet) on the mat and then determines whether the signal quality has improved. The control unit may direct the user to make multiple adjustments and then ask the user to adopt the position that was associated with the best signal quality. The control unit may be configured to present such directions to the user by means of screen 126, which may or may not form part of the mat 105.

It is advantageous if shape memory foam, whether low density or high, provides the surface of mat 105 in the region in which the hands or feet are configured to engage with the electrodes. This allows the mat to mould to the shape of the user's hands or feet and helps to reduce tremors and the effect of signal noise due to the vibration or movement of the hands or feet. The support provided by memory foam is of particular importance for users with certain conditions, such as rheumatism or certain neurological conditions.

Preferably the shapes of hands or feet are initially imprinted into high density memory foam to provide a guide as to how users should place their hands on the mat. Alternatively low density foam may be used to mould the foam around the users hands and thus provide a temporal support. Such hand-shaped or feet-shaped depressions in the memory foam could serve as the sets of indicia discussed above that indicate where on the mat the user is intended to place their hands or feet. The electrodes 101, 102 are preferably embedded in the memory foam with their conducting surface exposed for engagement with the user. The electrode surface is preferably level with the surface of the memory foam or slightly below the surface of the memory foam such that when the foam is compressed the hand/foot engages with the sensor. A suitable memory foam is Veriltye®, manufactured by the Cornerstone Research Group, Inc.

Note that in the case that electrodes 101, 102 are conducting electrodes, the mat could further comprise additional EP sensors. In particular, it can be advantageous if the EP sensors are encircled by the conductive electrodes such that the conductive electrodes can act as a grounding plate for the EP sensors. This allows control unit 112 to switch between the using the electrode and the EP sensor (in which the electrode is a grounding plate for the sensor) so as to acquire the best quality signal, or to better identify particular characteristics of the user's ECG.

The conductive region would preferably be arranged around each EP sensor such that the conductive region is in contact with the user when the user is engaged with the EP sensor. The conductive region is preferably grounded relative to the signal processing electronics of the mat and could be earthed if the mat is itself earthed. The conductive region is preferably a metal, such as copper. The conductive region could be in the form of a conductive ring with the EP sensor at the centre of the ring whose location is indicated by optional element 309 in FIGS. 3 (a) and (b)—note that if conductive ring 309 is present, electrode 303 would be an EP sensor. The conductive region could form at least part of the indicia arranged to indicate to the user how they are to engage with the mat.

The device optionally includes a camera 131. The output from the camera can be fed to the control unit so as to allow the control unit to interactively instruct the user as to the optimal placement of their hands. An optional mirror 132 may also be provided that can be configured to increase the camera's field of view.

The use of a camera 131 allows the position of the user's limbs on the mat relative to the electrodes to be monitored. The output of the camera is fed to control unit 112 which can be configured to direct the user to place their limbs in the optimal position. This may be in response to acquiring a poor quality signal. For example, the control unit may monitor by means of the camera the position of a user's hands on the mat. If the user's hands are not in the optimal position, the control unit could direct the user to improve their position by means of images or text on screen 126 that identifies to the user how their position might be improved. The camera could alternatively or additionally be used to identify movement of the user's hands such as tremors at the time of data acquisition. Artefacts in the signals from the electrodes that correspond to movement observed by the camera can be filtered from the signal using filtering algorithms well known in the art.

The provision of a camera 131 may alternatively allow the control unit to adapt its processing of the acquired ECG signals in dependence on the position of the user's limbs as detected by the camera relative to the electrodes. A mirror 132 may also be provided at the mat so as to allow the camera to identify the position of a user's limbs at points that are not visible by direct line of sight from the camera aperture. Alternatively or additionally the camera could have multiple apertures and sensors, or there could be multiple cameras 131.

Figure 3:
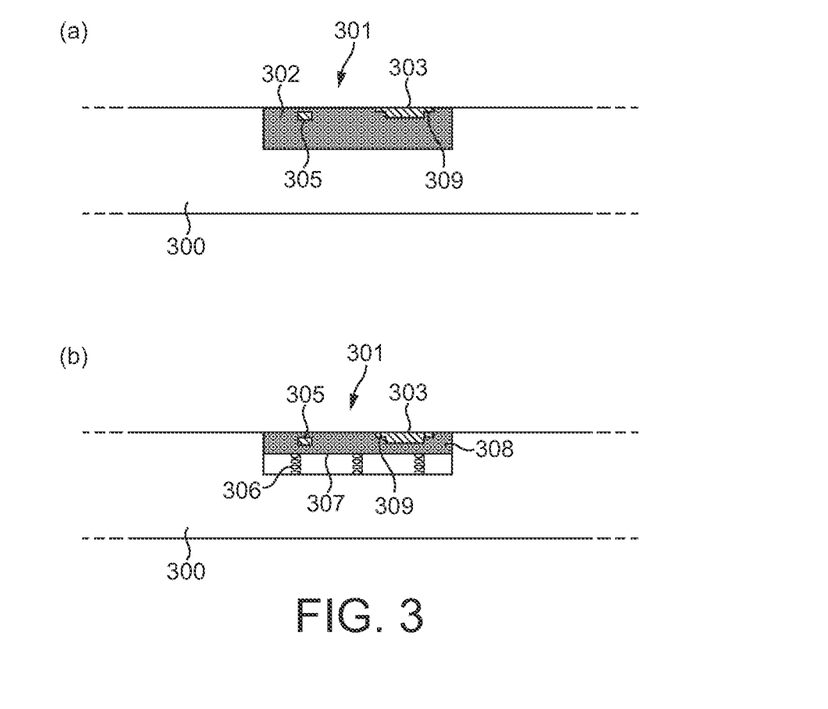
FIG. 3 illustrates schematic diagrams of two preferred embodiments of an ECG mat in accordance with the present invention.

A preferred embodiment of the invention is shown in FIG. 3. It is advantageous if the user interaction region 301 of the surface of the mat 300 with which the user engages their hands or feet is provided with one or more accelerometers 305 configured to detect the movements and vibration of the user's hands/feet. This is advantageous because of the high amplification of signals from the electrodes which means that the resulting signals are sensitive to small variations in electrode to skin contact resistance, as might be cause by movement or vibrations of a user's hand or foot. Such movement/vibration can result in variation of the DC content of the amplified differential signal from a pair of electrodes and typically manifests itself as a drift in the baseline of the ECG (often termed baseline wandering).

Most preferably the user interaction region of the surface of the mat is decoupled from the rigid body of the mat. For example, in FIG. 3(a) the user interaction region of the surface of the mat comprises a compressible foam 302 in which the electrodes are supported (such as the memory foam described above), or in FIG. 3(b) the user interaction region is a floating plate 307 decoupled from the rigid body of the mat by means of one or more springs, elastic compressible materials such as rubber, or any other kind of resilient couplings 306.

In the case in which the user interaction region is a floating plate, the electrodes 303 would be supported at the floating plate. The floating plate could itself support a compressible foam 308, such as a memory foam. The one or more accelerometers 305 could be located at the floating plate or could be configured to measure motion of the floating plate relative to the rigid body of the mat—for example, by means of one or more strain gauges connected between the mat and floating plate. If a compressible foam is used in the user interaction region of the surface of the mat, whether the foam is atop a floating plate or not, the accelerometers 305 would preferably be embedded in the portion of the compressible foam close to the surface with which the user's hands or feet engage. Accelerometers 305 could be any kind of accelerometer, such as a tilt sensor, piezoelectric accelerometer, capacitive accelerometer, or micro electro-mechanical (MEMS) device.

Preferably each user interaction region comprises at least one accelerometer. Most preferably the user interaction regions of a mat are decoupled from one another in that each region is a distinct region of compressible foam supporting one or more electrodes, or each surface region is independently supported at a floating plate. FIGS. 3 (*a*) and (*b*) each show a single user interaction region, thus electrode 303 might correspond to sensor 101 of FIG. 1 with region 301 corresponding roughly to the area indicated by one of the hands in FIG. 1. Typically each user interaction region corresponds to a particular point of interaction with the user, such as a hand or a foot.

Vibrations and movement of the user introduces noise into the signal detected by electrodes 303. By providing accelerometers 305, the effect of this noise on the electrode signal can be mitigated and the quality of signal improved. The output of accelerometer 305 provides a measure of the vibration and movement of the respective body part of the user that is engaged with the user interaction region 301. The accelerometer output can therefore be used to filter out corresponding variations in the signal from electrode 303 that are likely to be due to noise induced by the vibrations and movement of the user. Various algorithms could be used to achieve this. For example, when significant movement is detected by an accelerometer (or by the camera, as described above), variations in the signal from the corresponding electrode could be suppressed; and any periodic variations above a predetermined frequency (preferably around 30-100 Hz) present in both the output from the accelerometer and the electrode signal could be filtered from the electrode signal. This is particularly important in order to allow the system to identify uneven artefacts in the T-P wave part of the ECG that are suggestive of atrial fibrillation. Filtering algorithms for removing or suppressing features in a first signal (the ECG) that correlate with features in a second signal (the accelerometer output) are well known in the art.

It can be advantageous to use any EP sensors of the mat with which the user is not engaged (e.g. sensors 103 and 104 of FIG. 1) to measure movement or vibration of the user. Since the user is not engaged with those sensors, they will not pick up the ECG of the user. However, the EP sensors will to some extent act like microphones and this signal can be used in the filtering algorithms to remove or suppress the effect of vibrations from the ECG signal. In alternative embodiments, dedicated EP sensors or one or more microphones could be provided for this purpose instead or in addition to one or more accelerometers.

The output of one or more accelerometers, microphones or cameras configured to detect movement of the user could be stored with captured ECG data for later analysis. Data captured at the mat could be uploaded to an internet server (i.e. the "cloud") for more detailed analysis at more powerful servers or to allow a cardiologist to review the ECG trace— this could be requested by the patient or healthcare professional at the mat or control unit.

Figure 4:
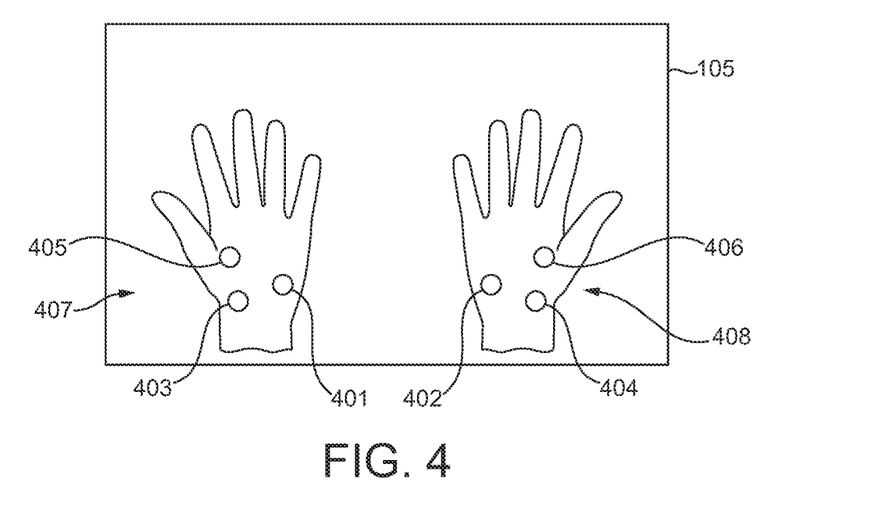
FIG. 4 is a schematic diagram of an ECG mat configure in accordance with the present invention and having multiple sensors at each user interaction region.

Some users may suffer from conditions that make it difficult to place their hands/feet in the intended manner on the user interaction regions of the mat. For example, users with advanced rheumatoid arthritis may find it difficult to lay their hands even roughly flat on the mat such that the electrodes lie directly under the balls of their thumbs. For such users it is preferred that the mat is configured to have indicia that indicate to the user a secondary hand position (not shown in FIG. 1) in which the hypothenar eminence (the fleshy part of the medial side of the hand) is located over electrodes 101 and 102. A second set of indicia need not be required if, as shown in FIG. 4, the mat provides multiple sensors per hand and the mat provides a mode in which it uses only those electrodes under the hypothenar eminence when the user places their hands as best they can on the mat. Such a mode would preferably be selectable by the user or a healthcare professional to indicate to the mat that the user cannot place their hand in the optimal, primary hand position.

In order to improve the quality of the ECG signal captured for such users, it is advantageous to provide a plurality of electrodes for engagement with the user at each user interaction region—i.e. a plurality of electrodes is provided for engagement with each hand or foot. By choosing the pair of outputs from a pair of user interaction regions that provide the cleanest signal, a mat configured according to a preferred embodiment of the present invention can maintain acceptable signal quality for a wide range of orientations of the user's hands and/or feet.

In order to select the optimum pair of electrode outputs, the differential signals can be calculated for each of the possible combinations of a plurality of electrodes at a first user interaction region with a plurality of electrodes at a second user interaction region. The quality of those signals can then be established by means of a QRS detection algorithm as described above. For example, with reference to FIG. 4, each of the outputs from electrodes 401, 403 and 405 at the first user interaction region 407 is paired with each of the outputs from electrodes 402, 404 and 406 at the second user interaction region 408 so as to form a set of 9 differential outputs $d_1$ to $d_9$ as set out in Table 1 below.

| Electrode | 402 | 404 | 406 |
| --- | --- | --- | --- |
| 401 | $d_1$ | $d_2$ | $d_3$ |
| 403 | $d_4$ | $d_5$ | $d_6$ |
| 405 | $d_7$ | $d_8$ | $d_9$ |

In some embodiments, only a subset of the possible differential outputs could be calculated so as to generate, for example, only those differential outputs that have been found to provide acceptable quality ECG signals. This can help to avoid unnecessary processing of the electrode outputs. In a preferred embodiment, the mat determines the signal quality of the differential signal from pairs of electrodes in turn and in a predetermined order until a minimum predetermined signal quality is achieved. If, once a predetermined series of electrode pairs has been tested and the minimum signal quality has not been achieved, the mat can move onto combinations of electrode pairs as described below, or could indicate to the user to change their position of engagement with the mat.

In preferred embodiments, the outputs of two or more electrodes at each user interaction region can be combined so as to minimise the effect of noise and allow the system to cope with sub-optimal placement of the user's hands or feet on the mat (which could, for example, be due to a medical condition afflicting the user). An average of the signals of a plurality of electrodes could be calculated for use as the electrode signal from the respective user interaction region. Preferably the average is a weighted mean to which the contribution having the greatest weight is from an electrode positioned such that it engages with thenar eminence or hypothenar eminence (in the case of a hand) or the heel of the foot (in the case of the foot). The weighting applied to these EP sensors which typically yield the best ECG signal is preferably at least 50% more than that of any other electrode.

Generally the electrode pairs that provide a differential signal from which the ECG is identified comprise two sensors of the same type: for example, in the case of hands if the first sensor of the pair is a sensor under the ball of the thumb (thenar eminence) of the left hand then the second sensor of the pair would be a sensor under the ball of the thumb of the right hand. However, this need not be the case and the differential signal could be obtained from an electrode from one part of the left hand (e.g. under the ball of the thumb) and an electrode engaged with a different part of the right hand (e.g. the hypothenar eminence).

A mat configured in accordance with the present invention can reliably capture a good quality ECG of more than 10 seconds duration within around 60 seconds. Within the capture period, the electrode pairs from which the ECG signal is captured could change in order to maintain a clean ECG.

Preferably the mat further comprises one or more additional EP sensors or electrodes 103, 104 that are provided as thin discs connected to the mat by wired or wireless means. These sensors can be used in various ways. Firstly, these sensors can be readily used to provide Lead II and III inputs to the mat: the user could place one or more of the free EP sensors or electrodes underneath their feet (e.g. they could stand on them), or the EP sensors/electrodes 103, 104 could be provided with a strap (e.g. a velcro strap) or other attaching means to attach them to the ankles or feet of the user. Secondly, the sensors/electrodes could be used by patients that have trouble engaging with the mat due to problems placing their hands roughly flat on the mat surface: the free sensors/electrodes could be simply held by the user or strapped to their hand (e.g. by means of a velcro strap) such that the sensor/electrode is directed to one of the preferred fleshy parts of their hand (i.e. the thenar eminence or the hypothenar eminence). Input means to the mat can allow the user or a medical professional to indicate to the mat which part of the body the electrodes are engaged with so as to allow the mat to properly process the acquired ECG.

The present invention is not limited to the detection of electrocardiographic (ECG) signals and could also be used for the detection of electromyographic (EMG) signals, i.e. the acquisition of electrical activity due to skeletal muscles. If camera 131 is present, it can be used to direct the user to place their limb in the optimal position for acquisition of the EMG signals of interest. For example, the control unit 112 could be configured to monitor the position of a user's forearm relative to electrodes of the mat and direct by means of screen 126 the optimal placement of the forearm over those electrodes in order to acquire a wrist muscle EMG. This can be achieved by causing a user to contract the particular muscle of interest, acquiring the EMG of that muscle or muscle group and comparing the characteristics of the EMG with a set of characteristics stored at data store 118. If the characteristics of the EMG suggest that the user's body part is not optimally positioned, the device can indicate to the user to reposition their body part. The device preferably indicates to the user the optimal position they should adopt.

By the provision of multiple sensors, the mat could be configured to acquire both ECG and EMG signals simultaneously. A system that incorporates the electrodes with an active feedback loop may have benefits in systems not necessarily for medical usages, such as sports and gym equipment. Understanding the muscle EMG coupled with a cardiac ECG might allow an exercise programme to be controlled for the limited exercising of specific muscle groups as analysed by the EMG, and with positive feedback being given to the subject by means of the camera and screen.

Electrodes can be made much smaller than human hands or feet. Multiple electrodes can therefore be allocated for each human limb. Through the use of statistical averaging over the electrodes allocated to a limb (e.g. hand or foot) a cleaner signal can be acquired and in a shorted space of time.

Figure 2:
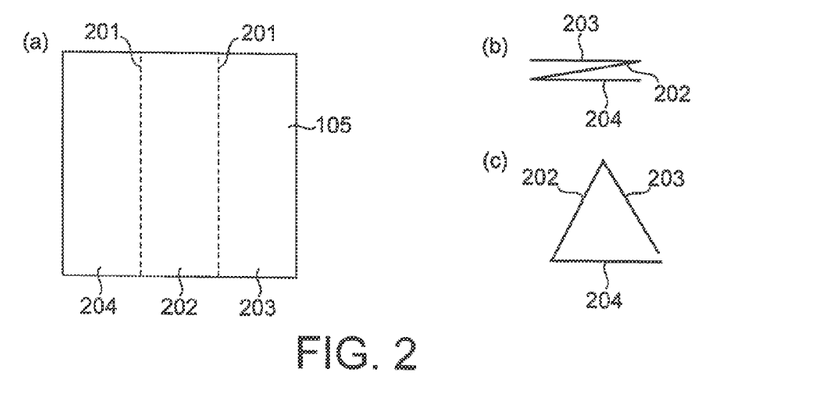
FIG. 2 is a schematic diagram of a foldable ECG mat configured in accordance with the present invention.

Electrocardiograph device 105 may be configured to be foldable along folds 201 as illustrated in FIG. 2. This can have two benefits. Firstly, as shown in FIG. 2(b), the mat can then be stored more compactly. Secondly, as shown in FIG. 2(c), the mat can be folded into a three-dimensional object: for example, a tubular object of triangular cross-section as shown in figure (c), or a tubular object of rectangular cross-section if the mat were to have three folds 201. In FIG. 2(c), the folds of the mat are configured such that the surfaces of the mat comprising the electrodes 202, 203 are presented to a user when the mat is rested on a third surface 204. Such a folding arrangement might allow the mat to be used more comfortably when an ECG signal is acquired from a pair of hands or any other body part.

Figure 5:
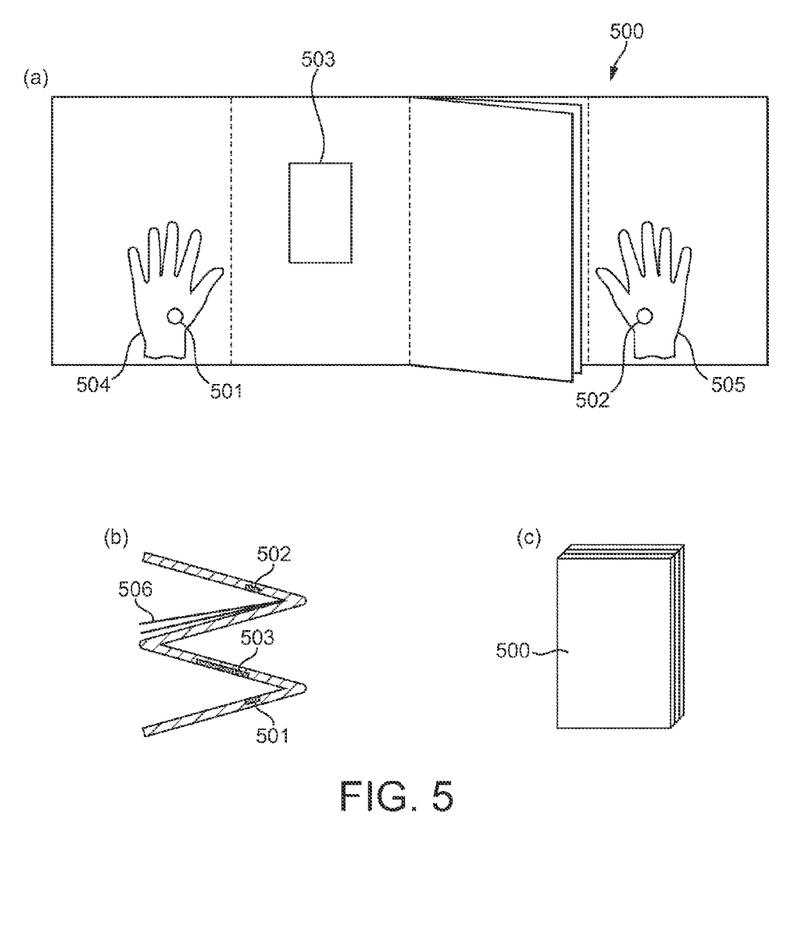
FIG. 5 is a schematic diagram of an ECG mat configured in accordance with the present invention and provided in the form of a book.

A further embodiment of the present invention is shown in FIG. 5, in which electrocardiograph device 500 is provided in the form of a book having electrodes 501, 502 on the inside front and back covers. Indicia 504, 505 can be provided to indicate to a user how to arrange their hands on the book. The book could comprise a processor (not shown) and a touchscreen 503. The book comprises one or more pages 506 that preferably explain to the user how to use the device. FIG. 5(a) shows the device when opened out flat for use, FIG. 5(b) shows the device in a partially-folded position, and FIG. 5(c) shows the device when fully folded up as a book. This embodiment provides the electrocardiograph device in a convenient form that is particularly suitable for use in the home or office, and allows the ECG to be readily stored in a form that is not obviously a medical device.

The ECG signals acquired by the electrodes of the mat are analysed at control unit 112 and/or a coupled data processing unit. By comparing the signal acquired at one electrode with that acquired at another electrode according to a common time base, the various leads of an ECG system can be determined and derived as is known in the art. The control unit 112 and/or a coupled data processing system may be able to run any form of digital analysis on the acquired ECG data, such as algorithms for arrhythmia detection.

The ECG signal could be cleaned up by analogue or digital electronics at drive stage 116. Digital samples are preferably captured at between 1 and 5 kHz.

As described above, a QRS detection algorithm is used to identify the basic features of the ECG signal from the differential output of a pair of electrodes. Further algorithms can then be used to identify various characteristics of the ECG and it is possible to analysis an ECG signal from more than one starting point. For example, a P wave algorithm analyses the signal by detecting the presence of the P wave, whereas an R-R algorithm analyses the signal by detecting the R-R interval in the ECG signal. Generally, either type of algorithm can be used in the analysis of an ECG.

It is advantageous if the mat is configured to utilise one of the types of algorithm in dependence on an initial parse of the ECG signal (which could be performed by the QRS detection algorithm). If the initial signal shows a high amplitude signal has been recorded then there is a high probability that the system should be able to detect a strong P wave should it exist. Preferably, if the amplitude of the QRS complex in the detected signal is greater than the noise floor by a predetermined value (e.g. equivalent to 0.8*S wave amplitude in V1+R wave amplitude in V5<3.5 mV for a conventional ECG), then a P wave algorithm is used. Otherwise an R-R interval algorithm is used.

Suitable P wave detection algorithms include those described in "Detection of P and T-waves in Electrocardiogram" by S. S. Mehta and N. S. Lingayat, Proceedings of the World Congress on Engineering and Computer Science 2008, San Francisco, USA and "Characteristic wave detection in ECG signal using morphological transform" by Yan Sun et al., BMC Cardiovascular Disorders Vol. 28, Issue 5, 2005.

A suitable R-R interval detection algorithm is described in "A simple method to detect atrial fibrillation using RR intervals" by Lian et al, American Journal of Cardiology, Vol. 107, Issue 10, 2011.

Suitable QRS detection algorithms are described in "Quantitative investigation of QRS detection rules using the MIT/BIH arrhythmia database", IEEE Transactions on Biomedical Engineering, Vol. BME-33, No. 12, 1986.

It can be further advantageous to indicate to the user when the ECG captured by the differential output of a pair of electrodes (i.e. a one-lead ECG) is of poor quality. In particular, it is proposed that in preferred embodiments the mat is configured to indicate to the user (e.g. by means of screen 126) that the captured signal is of poor quality and that the user should therefore move to using a three-lead ECG configuration by utilising an additional mat coupled to the first mat. For example, if the first mat is configured to receive inputs from a user's hands, the mat could indicate to the user to additionally engage with a mat configured to receive inputs from one or more of the user's feet. By combining the outputs of the respective electrodes at one/both of the mats or at an external or remote control unit connected to the mats (such as a laptop) a three-lead ECG can be calculated.

By directing the user to engage with the ECG monitoring system of the present invention in this manner, the system aims to ensure that the captured ECG is of sufficient quality to ensure that the sensitivity and specificity values of the P wave and R-R interval algorithms can be maintained, thus increasing the confidence factor of the system.

It can also be advantageous to arrange that specific biomarkers other than the ECG are carried in the signals from the electrodes and not removed by filtering. Thus not only the ECG signal may be encoded but also additional signals from different muscle groups (or other anatomical entities). If the control unit cannot itself process such additional signals, they can be stored by the control unit for later analysis.

Screen 126 may be used to give feedback to the subject with regards the duration that the subject should keep their limbs engaged with the surface. In such a manner if the control unit that received the data from the plurality of electrodes and passed this to data to an algorithm to analyse, and subsequently the algorithm identified that the user had a known problem with their physiological data, then the system, through the screen could inform the subject to extend their testing period for a known period of time, such that the condition identified may be verified by taking a longer reading of physiological data over a longer period of time, thus reducing the potential for false positive analysis.

The present system can be utilised to take a quick ECG reading through limb placement over a multitude of electrodes and lends itself to being able to provide a quick ECG analysis of current cardiac performance. Even over a time period of perhaps only 90 seconds it may well be possible to not only run an algorithm on the system to detect arrhythmia and other well documented cardiac conditions, but also to export the statistics of each cardiac or physiological parameter recorded, and then to calculate the average or median performance of each physiological cycle. Such data can be used in the control inputs of a medical scoring system, such as the Karnofsky, Zubrod, Apache III, or Geneva scoring systems.

Where specific physiological monitoring scoring systems exist for say cardiology, it may be possible to identify a risk stratification for the subject based on the output performance characteristics of their sinus rhythm with regards the time span that they were monitored by the electrodes. In such a manner it may well be possible to extrapolate a whole series of performance indices, such as average QRS complex time. Such indices can be provided with the ECG traces themselves at the output 129 of the control unit, and/or at screen 126. These indices, coupled with any artefacts identified by the unique to subject start up sequence acquired by each electrode, can yield artefacts for further analysis which can be output from the control unit.

The data from electrodes may be transmitted over link 110 in a high level format such as XML or HL7. Preferably timestamps are encoded into such a high level stream format, along with optionally an indication of location of the parts of the anatomy being monitored/the location of electrodes on a subject's body. This may prove beneficial in the production of body mapped electrical systems activity and subsequent multi-dimensional imagery through the utilisation of a plurality of sensor, perhaps in the region of 120 electrodes in a system to wrap and encompass the upper torso of the human body. Such a system could be incorporated into a shirt or other clothing offering.

The output of the source ECG signal that has been acquired from the limb placement upon the electrodes, may well be output in a high level format such as HL7, XML, etc, in such a manner that the original source ECG trace may be available for analysis in conjunction with any events that caused arrhythmias to be identified already correlated to the source ECG trace. In a similar manner any identified other physiological parameters identified may also be included in the analysis.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. An electrocardiographic device for sensing cardiac activity in a user, the electrocardiographic device comprising:
    a plurality of electrodes provided at a surface of the device for electrical engagement with the hands of a user;
    a set of indicia indicating an intended position for a user's hands on the device, the set of electrodes being arranged relative to the set of indicia such that, in use when a user's hands are in the intended position, at least one electrode is located under the thenar eminence of each of the user's hands;
    one or more movement sensors arranged to, in use, detect movement of a user's hands; and
    a control unit configured to receive electrical signals from the electrodes and to, in use, process said signals in dependence on the output of the one or more movement sensors so as to filter variations from the signals due to movement of the user's hands.

2. An electrocardiographic device as claimed in claim 1, wherein the plurality of electrodes comprises a first set of one or more electrodes for engagement with a first hand of a user and a second set of one or more electrodes for engagement with a second hand of a user, the first set of electrodes having an associated first movement sensor arranged to detect movement of the first hand and the second set of electrodes having an associated second movement sensor arranged to detect movement of the second hand, the control unit being configured to perform filtering of signals from the first and second sets of electrodes in dependence on the output from the respective movement sensor.

3. An electrocardiographic device as claimed in claim 1, wherein said filtering comprises cancellation or suppression of features in electrical signals from the electrodes that are common to both the signals from the electrodes and the output of the one or more movement sensors.

4. An electrocardiographic device as claimed in claim 1, wherein the control unit is configured to provide said filtered electrical signals at an output of the device.

5. An electrocardiographic device as claimed in claim 1, wherein the output of the one or more movement sensors represents motion and/or vibration of the user's hands.

6. An electrocardiographic device as claimed in claim 1, wherein the one or more movement sensors include one or more of an accelerometer, a strain gauge, a microphone and a pressure sensor.

7. An electrocardiographic device as claimed in claim 1, wherein the electrodes of the set are provided at two electrically insulating user interaction regions of the electrocardiographic device, each user interaction region being adapted for engagement with a hand of a user.

8. An electrocardiographic device as claimed in claim 7, wherein each user interaction region comprises a layer of shape memory foam for engagement with a user's hand, the electrodes being provided at the shape memory foam.

9. An electrocardiographic device as claimed in claim 7, wherein each user interaction region is supported on a floating plate elastically coupled to the body of the electrocardiographic device.

10. An electrocardiographic device as claimed in claim 9, wherein each user interaction region is coupled to the body of the electrocardiographic device by a damping mechanism arranged to dissipate kinetic energy due to motion of the floating plate relative to the body of the electrocardiographic device.

11. An electrocardiographic device as claimed in claim 9, wherein both user interaction regions are supported at the same floating plate.

12. An electrocardiographic device as claimed in claim 9, wherein each floating plate is elastically coupled to the body of the electrocardiographic device by one or more of: elastic springs, resilient rubber or plastic members, and elastic foam.

13. An electrocardiographic device as claimed in claim 1, wherein the indicia comprise a graphical pair of hands indicating the intended position of a user's hands relative to the electrodes and/or indentations on the surface of the device indicating the intended position of a user's hands relative to the electrodes.

14. An electrocardiographic device as claimed in claim 1, further comprising a second set of indicia indicating a second intended position of a user's hands with respect to the electrodes; wherein the electrodes are arranged relative to the second set of indicia such that, in use when a user's hands are in the second intended position, at least one electrode is located under the medial side of the hypothenar eminence of each of the user's hands.

15. An electrocardiographic device as claimed in claim 1, wherein the set of electrodes of the device are provided for electrical engagement with the feet of a user and the device comprises a set of indicia indicating an intended position for a user's feet on the device, the set of electrodes being arranged relative to the set of indicia such that, in use when a user's feet are in the intended position, at least one electrode is located under the heel pad of each of the user's feet.

16. An electrocardiographic device as claimed in claim 1, further comprising a display screen operable to display an electrocardiograph acquired by the electrodes.

17. An electrocardiographic device as claimed in claim 1, wherein the electrocardiographic device is configured to be foldable along one or more folds such that, when folded, the device is operable to present at least one of the electrodes on each of two outward-facing surfaces of the device, the two outward-facing surfaces being separated by at least one fold.

18. An electrocardiographic device as claimed in claim 17, wherein the electrocardiographic device is provided in the form of a book having one or more pages, at least one of the electrodes being provided at the front and rear inside covers of the book.

19. An electrocardiographic device as claimed in claim 18, wherein the pages of the book provide instructions for use of the electrocardiographic device.

20. An electrocardiographic device as claimed in claim 1, further comprising one or more inputs for receiving signals from wearable electrodes, the control unit being operable to combine said one or more inputs with the signals from the set of electrodes so as to form representations of one or more multi-lead ECGs.

21. An electrocardiographic device as claimed in claim 20, wherein the inputs are wired or wireless inputs.

22. An electrocardiographic system comprising:
a first electrocardiographic device including:
a plurality of electrodes provided at a surface of the device for electrical engagement with a pair of hands of a user;
a set of indicia indicating an intended position for a user's hands on the device, the set of electrodes being arranged relative to the set of indicia such that, in use when a user's hands are in the intended position, at least one electrode is located under the thenar eminence of each of the user's hands;
one or more movement sensors arranged to, in use, detect movement of a user's hands; and
a control unit configured to receive electrical signals from the electrodes and to, in use, process said signals in dependence on the output of the one or more movement sensors so as to filter variations from the signals due to movement of the user's hands; and
a data processing unit configured to process signals from the electrodes of the first electrocardiographic device so as to form an electrocardiogram and/or diagnose cardiac abnormalities.

23. An electrocardiographic system as claimed in claim 22, wherein the data processing unit is one or more of a personal computer, handheld computer, smartphone, server, or a processing unit of the electrocardiographic device itself.

24. An electrocardiographic system as claimed in claim 22, wherein the electrocardiogram is a Lead I electrocardiogram.

25. An electrocardiographic system as claimed in claim 22, wherein the electrocardiographic system further comprises one or more wearable biosensors and the data processing unit is further configured to process signals from the wearable biosensors so as to form an electrocardiogram in dependence on signals from both the wearable biosensors and the electrodes of the first electrocardiographic device.

26. An electrocardiographic device as claimed in claim 25, wherein the wearable biosensors are electric potential sensors or conducting electrodes.

27. An electrocardiographic system as claimed in claim 25, wherein the wearable biosensors are provided in clothing and/or as straps adapted for engagement with a limb or extremity of a user.

28. An electrocardiographic system as claimed in claim 22, wherein the electrocardiographic system further comprises a second electrocardiographic device, and the data processing unit is further configured to process signals from the electrodes of the second electrocardiographic device so as to form an electrocardiogram in dependence on signals from electrodes of both the first and second electrocardiographic devices, wherein the second electrocardiographic device includes:
   another plurality of electrodes provided at a surface of the device for electrical engagement with a pair of extremities of a user;
   one or more additional movement sensors arranged to, in use, detect movement of a user's extremities; and
   another control unit configured to receive electrical signals from the one or more additional electrodes and to, in use, process said signals in dependence on the output of the one or more additional movement sensors so as to filter variations from the signals due to movement of the user's extremities.

29. An electrocardiographic system as claimed in claim 28, wherein the electrocardiogram includes a Lead II and/or III electrocardiogram.

30. An electrocardiographic system as claimed in claim 22, wherein the data processing unit is configured to characterise an electrocardiogram according to a predetermined set of cardiac parameters, including one or more of: amplitude and duration of a detected QRS complex, ventricular activation time, relative amplitude and timings of the Q, R and S peaks, R-R interval, QT interval, P wave timing relative to the QRS complex, and T wave to P wave smoothness.

31. An electrocardiographic system as claimed in claim 30, wherein the data processing unit is configured to diagnose cardiac abnormalities in dependence on the predetermined set of cardiac parameters.

32. An electrocardiographic system as claimed in claim 31, wherein the data processing unit is configured to diagnose cardiac abnormalities in dependence on a comparison of the cardiac parameters of the electrocardiogram with a set of stored cardiac parameters.

33. An electrocardiographic system as claimed in claim 22, wherein the data processing unit is configured to, on detecting one or more features indicative of cardiac abnormalities in the electrocardiogram, provide the electrocardiogram to a healthcare professional for further analysis and/or indicate to the user that the advice of a healthcare professional should be sought.

34. An electrocardiographic system as claimed in claim 22, further comprising a data store accessible to the data processing unit, the data processing unit being configured to store the predetermined set of cardiac parameters at the data store and optionally a digital representation of signals from the electrodes along with, optionally, a digital representation of output(s) of the movement sensor(s).

35. An electrocardiographic system as claimed in claim 22, wherein the data processing system is configured to instruct the user to connect at least one wearable biosensor and/or a second electrocardiographic device if one or more of the following is true: one or more features characteristic of a cardiac abnormality are detected in the electrocardiogram; signals from the electrodes of the first electrocardiographic device or the electrocardiogram itself includes characteristics indicative of a poor signal; and one or more expected characteristics of cardiac activity are absent or only weakly present in the electrocardiogram, wherein the second electrocardiographic device includes:
   another plurality of electrodes provided at a surface of the device for electrical engagement with a pair of extremities of a user;
   one or more additional movement sensors arranged to, in use, detect movement of a user's extremities; and
   another control unit configured to receive electrical signals from the one or more additional electrodes and to, in use, process said signals in dependence on the output of the one or more additional movement sensors so as to filter variations from the signals due to movement of the user's extremities.

36. An electrocardiographic system as claimed in claim 35, wherein the expected characteristics of cardiac activity include a P wave.

37. An electrocardiographic system as claimed in claim 35, wherein the data processing unit is configured to instruct the user by means of a display screen at the first electrocardiographic device.

38. An electrocardiographic system as claimed in claim 22, wherein the first and second sets of electrodes of the first electrocardiographic device each comprise a plurality of electrodes and the data processing unit is configured to (i) form a measure of the quality of the differential signal from each pair of electrodes that includes one electrode from the first set and one electrode from the second set, and (ii) select that pair of electrodes that has the highest quality measure as the Lead I signal.

39. An electrocardiographic system as claimed in claim 22, wherein the data processing system is configured to process signals from the electrodes in accordance with a QRS detection algorithm and, if the amplitude of the QRS complex is determined to exceed the noise floor by greater than a predetermined amount then a P wave algorithm is used for subsequent analysis of the electrocardiogram, otherwise an R-R interval algorithm is used for subsequent analysis of the electrocardiogram.

* * * * *